United States Patent [19]

Matsui

[11] Patent Number: 4,494,933
[45] Date of Patent: Jan. 22, 1985

[54] ROTATION CONTROL DEVICE FOR DENTAL HANDPIECE

[75] Inventor: Takahiro Matsui, Uji, Japan

[73] Assignee: Kabushiki Kaisha Morita Seisakusho, Kyoto, Japan

[21] Appl. No.: 473,241

[22] Filed: Mar. 8, 1983

Related U.S. Application Data

[63] Continuation of Ser. No. 235,648, Feb. 18, 1981, abandoned.

[30] Foreign Application Priority Data

Feb. 19, 1980 [JP] Japan .................................. 55-21015

[51] Int. Cl.³ .............................................. A61C 1/02
[52] U.S. Cl. .......................................... 433/98; 91/38; 415/503
[58] Field of Search ................ 433/98, 99, 100, 27; 137/624.11; 60/394; 91/38; 415/51, 503

[56] References Cited

U.S. PATENT DOCUMENTS

| | | | |
|---|---|---|---|
| 3,384,344 | 5/1968 | Ota | 415/51 |
| 3,526,978 | 9/1970 | Jordan | 60/394 |
| 3,590,582 | 7/1971 | German et al. | 60/394 |
| 3,666,025 | 5/1972 | Hanson et al. | 91/38 |
| 3,732,934 | 5/1973 | Brandenberg | 415/51 |
| 3,850,078 | 11/1974 | Polizzi | 91/38 |
| 3,963,391 | 6/1976 | Thornburn et al. | 433/100 |
| 4,046,058 | 9/1977 | Grisebach | 137/624.11 |

Primary Examiner—John J. Wilson
Attorney, Agent, or Firm—Koda and Androlia

[57] ABSTRACT

This disclosure relates to a rotation control device for an air-drive and air-journal type dental handpiece, wherein rotation control is made by applying a braking force to an air journaled turbine for a certain time by the use of compressed air operated air timer and a closing valve. When the braking force is applied to cut off drive air to the turbine, there is produced negative pressure in the bearing mechanism by the inertial rotation of the turbine, whereupon negative pressure causes the turbine to suck dirt thereinto. There is also a danger of the operator being hurt by idle rotation of the cutting tool which is rotated together with the turbine. The device of the invention prevents effectively this kind of sucking up dirt and injury to operators.

1 Claim, 7 Drawing Figures

ROTATION CONTROL DEVICE FOR DENTAL HANDPIECE

This is a continuation of application Ser. No. 235,648, filed Feb. 18, 1981, now abandoned.

BACKGROUND OF THE INVENTION

1. Field of the Invention

This invention relates generally to a control device for controlling the rotation of a dental air bearing turbine and more particularly to a control device for controlling the rotation of an air bearing turbine designed to apply a braking force corresponding to a fixed amount of air to the air bearing turbine by use of an compressed air actuated timer and a closing valve.

2. Prior Art

A dental handpiece (hereinafter referred to as a handpiece) using a static pressure type air bearing is designed to journal a rotating shaft carrying a cutting tool by the static pressure air bearing and to rotate the cutting tool by blowing compressed air through an air nozzle onto the front of a turbine provided integral with the rotating shaft, and has heretofore employed means for stopping the supply of compressed air because the smallness of the bearing in size and capacity makes it impossible for the bearing to be subjected to a large braking load when stopping the rotation of handpiece. However, the control means of the kind described is not free from the disadvantage that the bearing is reduced in its performance as soon as the supply of compressed air is stopped but the rotating shaft and turbine continue rotating by inertia, say, for about 12 to 15 seconds and that because this inertial rotation of the turbine acts as a fan on the bearing, the interior of the bearing mechanism is subjected to negative pressure and the air outside the bearing mechanism is sucked along with the chippings powder, dust or the like suspending in the air into the bearing surface to thereby stain or roughen the bearing surface which requires very fine maintenance, resulting not only in the reduction of bearing performance but also in hurting a dental operator by possible contact with the cutting tool during inertial rotation. Accordingly, it is necessary that stop of rotation of the cutting tool should minimize the load on the bearing and should be able to be effected in the shortest possible period of time and that there should prevail no negative pressure inside the bearing mechanism. A detailed description is given of the known control device for handpiece (refer to Japanese Patent Publication No. 31519/1971) that meets such requirements with reference to the control circuit shown in FIG. 1. As apparent from FIG. 1, there are disposed three-way magnetic valves 4 and 5 within handpiece 1, the magnetic valves being connected by an air feed passage 2 and an exhaust passage 3, and the magnetic valve 4 includes passages 6, 7 and 8, a first valve not shown, a spring 10 and an electromagnetic coil 11.

The passage 6 communicates through a pipe 12 with a compressed air source 9, the passage 7 communicates with the air feed pipe 2, and the passage 8 communicates with the open air, the first valve normally blocking the passage 6 by the resilience of a spring 10. Accordingly, the passages 7 and 8 normally communicate with each other. However, when the coil 11 gets excited, the first valve is sucked and moved against the action of the spring 10, and as soon as the passage 6 is opened, the passage 8 is blocked and the passage 6 is brought into communication with the passage 7. A magnetic valve 5 is the same in structure as a magnetic valve 4 and comprises three passages 13, 14 and 15, a second valve not shown, a spring 17 and an electromagnetic coil 18. The passage 13 is connected to a pipe 19 connecting to a pipe 12 while the passages 14 and 15 communicate respectively with an exhaust passage 3 and with the open air. Since the second valve normally blocks the passage 13 by the spring 17, the passages 14 and 15 normally communicate with each other. However, when the coil 18 gets excited, the second valve is sucked and moved against the resilience of the spring 17 and as soon as the passage 13 is opened, the second valve blocks the passage 15, with the result that the passages 13 and 14 are brought into communication with each other.

When a switch 20 is operated in the state shown, a contact-maker 21 is brought into contact with a contact 23, and when the coil 11 gets excited, compressed air is supplied to an air supply passage 2 to thereby rotate a cutting tool. The air after having been used is exhausted to the open air through an exsaust passage 3, passages 14 and 15. When the contact-maker 21 is brought into communication with the contact 23, a coil 26 gets excited and capacitors 24 and 25 are charged. When the switch 20 is returned to its original state, the contact-maker 21 is also brought into contact with a contact 22, the coil 11 gets deexcited, an air feed passage 2 is brought into communication with a passage 8 to thereby communicate with the open air. And simultaneously therewith, a coil 18 is excited through an already closed main contact 28 of a delay relay 30, so that compressed air is supplied from a passage 19 to an exhaust passage 3 to thereby suddenly stop rotation of the cutting tool, which is being rotated by inertia and maintain the pressure in the bearing mechanism of a handpiece 1 higher than the open air. The electric current discharged from capacitors 24 and 25 is reduced in a certain period of time and the coil 26 of a delay relay 30 is deexcited to thereby return the relay 30 to its original state, with the result that the coil 18 is deexcited and the valve 5 is returned to its original position to thereby finish operation of the control device. However, in the rotation control device for the handpiece of the kind described above a delay relay 30 operated by the charging action of capacitors 24 and 25 is used. Accordingly the capacitors and advance in deterioration by repeated use and are widely different in discharging time, depending upon an atmosphere such as a temperature and humidity, and become unstable in delay time. As a result, the handpiece does not fully stop operation, or is reversely rotated by jetting of compressed air from an exhaust passage, to thereby damage the bearing, and even when it is desired to change relay time in accordance with the strength of air pressure to be used, change of relay time is impossible without replacement of capacitors. The disadvantages and inconveniences described above are inherent in the prior art braking system of dental handpieces.

SUMMARY OF THE INVENTION

The present invention has for its object the removal of the above described disadvantages and inconveniences inherent in the rotation control device for the conventional type dental air bearing turbine. In keeping with the principles of this invention, the objects are achieved by the unique structure including an air bearing journalling a rotating shaft supporting a dental cutting tool, a turbine provided integral with the shaft, an air passage for supplying the air bearing and turbine with compressed air and for exhausting the air used in the turbine, and a compressed air source; the rotation control device being characterized in that it includes a magnetic valve for connecting the air passage to the compressed air source, a closing valve for opening and closing the exhaust passage, and an air timer for controlling the closing valve.

BRIEF DESCRIPTION OF THE DRAWINGS

The invention will now be described in detail with reference to the accompanying drawings in which.

DETAILED DESCRIPTION OF THE INVENTION

Figure 1:
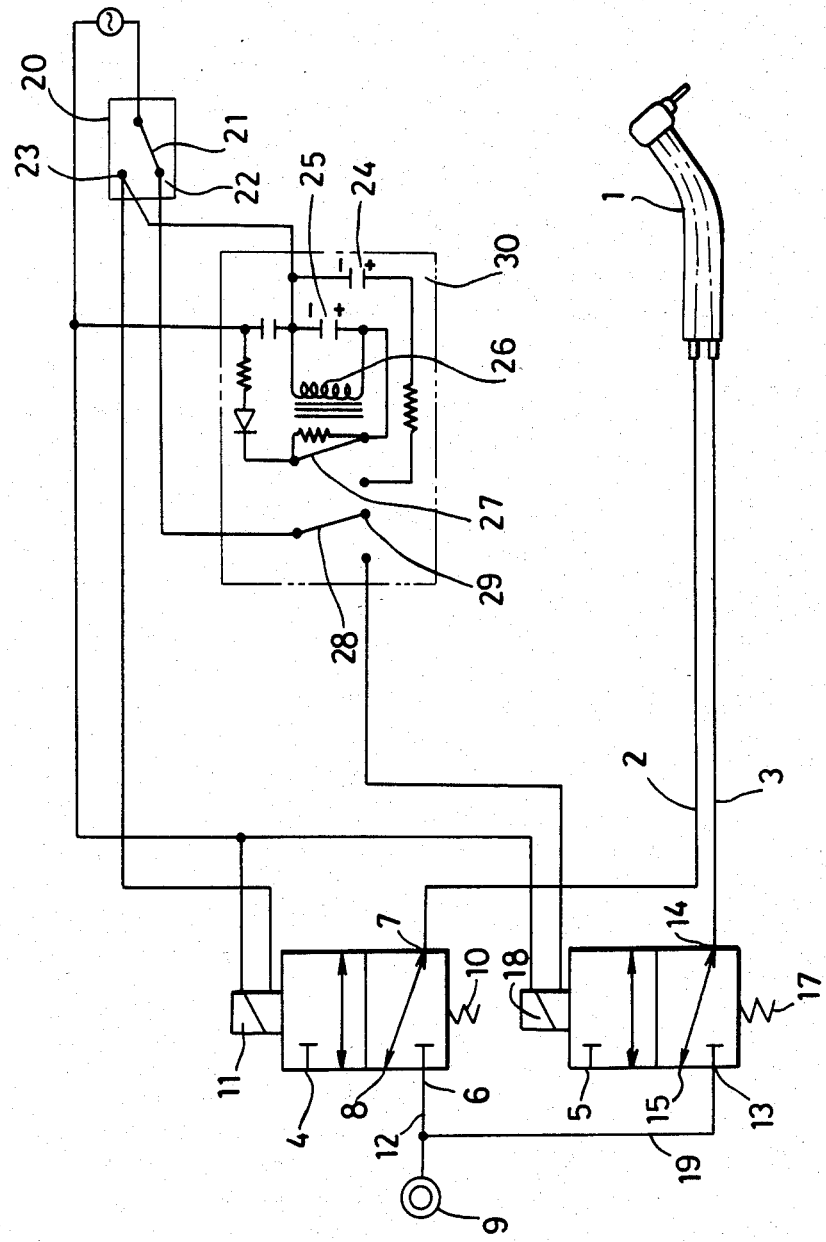
FIG. 1 is a circuit diagram showing rotation control of a conventional type dental air bearing turbine.
Figure 2:
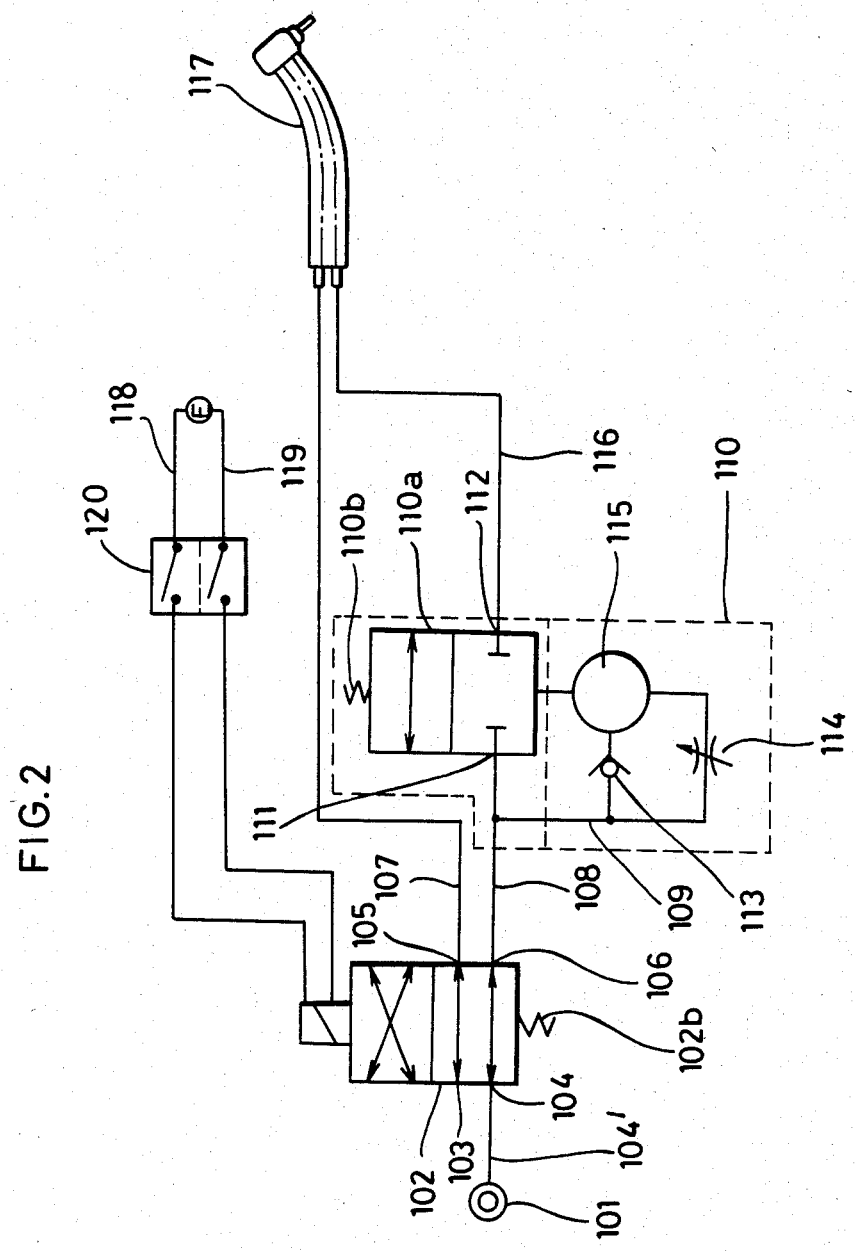
FIGS. 2 through 4 are circuit diagrams showing rotation control of a dental air bearing turbine embodied in one form of the invention.

In the drawings, the numeral 101 designates a compressed air source; 102 a four-way magnetic valve; 110 an air timer; 110a a closing valve provided in an exhaust passage 116; 117 a handpiece; and 120 designates a switch for controlling the four-way magnetic valve 102. The compressed air source 101 is connected to a passage 104 by a pipe 104'. In the state shown in FIG. 2, the passage 104' communicates with a passage 106 and a passage 103 communicates with a passage 105. Compressed air passes through the passages 104 and 106 of the four-way magnetic valve 102 and through a pipe 108, a pipe 109 of the air timer 110 and a throttle valve 114 to a tank 115. Accordingly, the passage 111 and passage 112 of the valve 110a are brought into a cut-off state by the internal pressure of the tank 115 so as to admit compressed air to an exhaust passage 116 connecting a handpiece 117 to the passage 112. On the other hand, no pressure is applied to an air passage 107 connecting a passage 105 to the bearing portion and turbine of handpiece 117, since the passage 103 communicating with passage 105 is open to the atmosphere.

Figure 3:
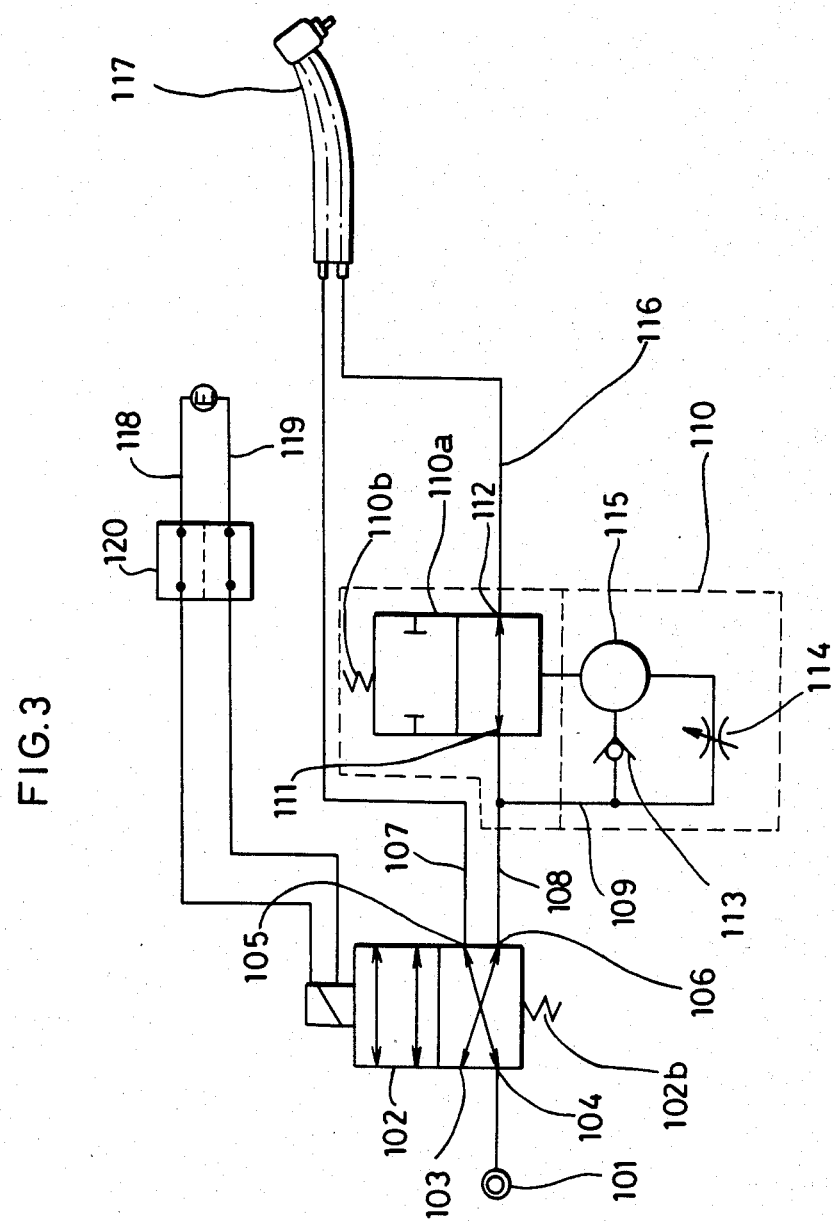

When a switch 120 is closed as shown in FIG. 3, connection is established between power sources 118 and 119 and a four-way magnetic valve 102, the magnetic valve 102 is opened, the passage 104 is brought into communication with passage 105 and the passage 103 is brought into communication with passage 106, the compressed air in the tank 115 passes through a return valve 113 and a throttle valve 114 and is instantaneously discharged from the passage 103 through pipes 109, 108 and a passage 106 into the open air, a valve 110a is changed over by the action of a spring 110b and communication is made between passages 111 and 112 to supply compressed air to the air bearing of the handpiece 117 through passages 104, 105 and air feed passage 107 and to rotate the turbine journalling a cutting tool. The air after having turned the turbine is discharged into the open air from the passage 103 through an exhaust passage 116, passages 112, 111, pipe 108 and passage 106.

Figure 4:
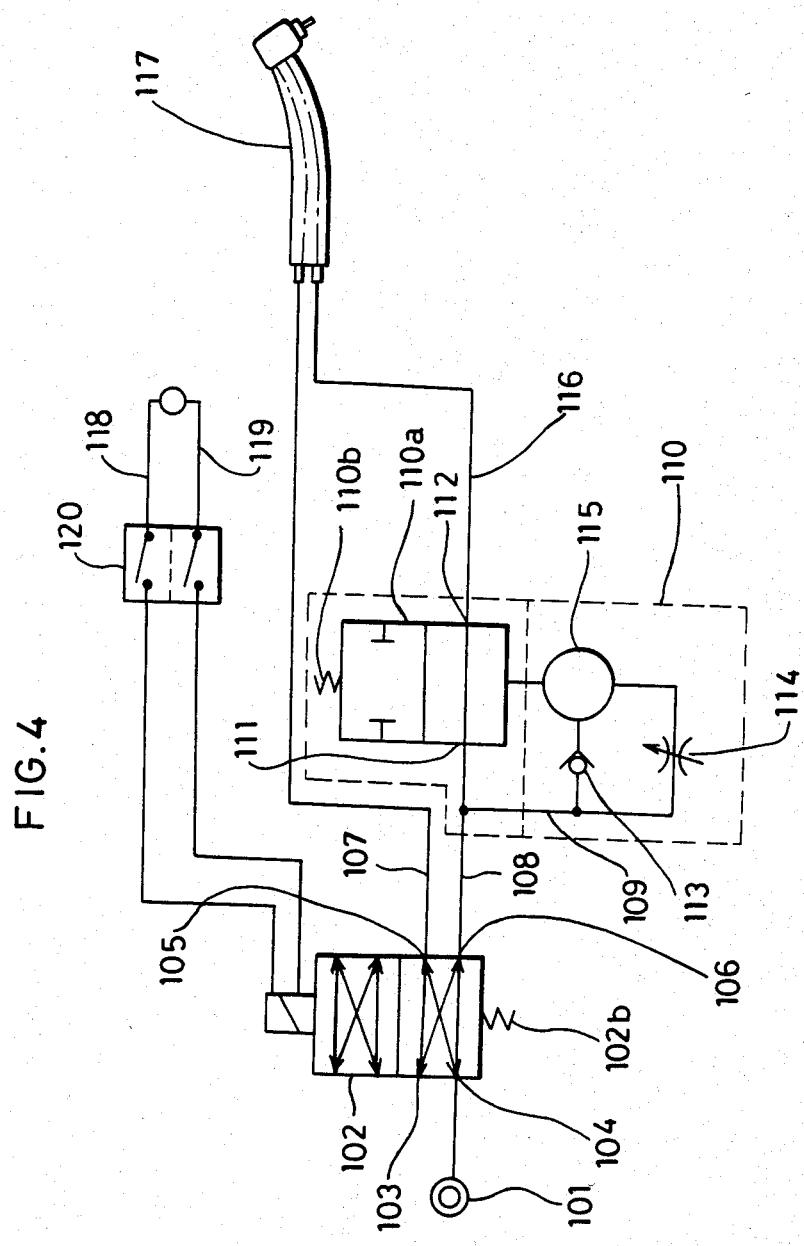

Now, when the switch 120 is released as shown in FIG. 4, the power supply lines 118 and 119 are cut off from a four-way magnetic valve 102, and the valve 102 is returned by the action of a spring 102b to thereby bring the passage 103 into communication with the passage 105 and bring the passage 104 into communication with the passage 106 to thereby supply compressed air to the passage 111 and pipe 109. However, in order to keep the pressure in the tank low so as to prevent the passage 111 from being cut off from the passage 112, compressed air is supplied from the exhaust passage 116 to the handpiece 117 to thereby quickly stop the turbine which is being rotated by inertia and to admit compressed air to a bearing mechanism, with the result that there is no possibility of the atmosphere being sucked into the bearing mechanism by the inertial rotation of the motor. The air after it has passed through the turbine is released into the open air from the passage 103 through the air feed passage 107 and passage 105. The compressed air supplied to the pipe 109 is gradually supplied to the tank 115 through a throttle valve 114. When the pressure in the tank attains a certain pressure, the air overcomes the force of spring 110b to thereby shut off the passage 111 from the passage 112 to bring about the state shown in FIG. 2 again. In other words, the area of the throttle valve 114 and capacity of the tank 115 determine the time at which compressed air is supplied to the exhaust pipe 116, namely the time for applying a brake to the turbine.

Figure 5:
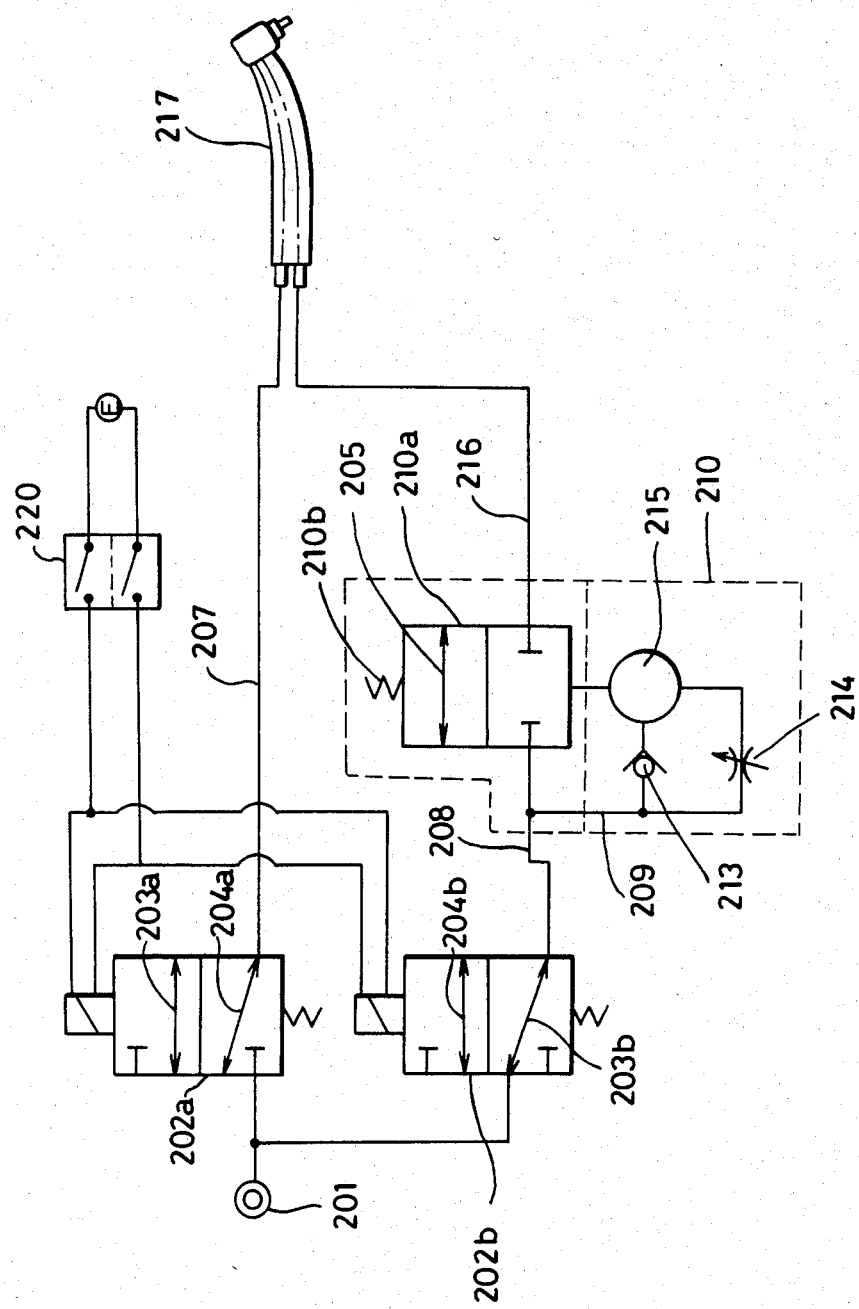
FIGS. 5 through 7 are circuit diagrams showing rotation control of a dental air bearing turbine embodied in another form of the invention.
Figure 6:
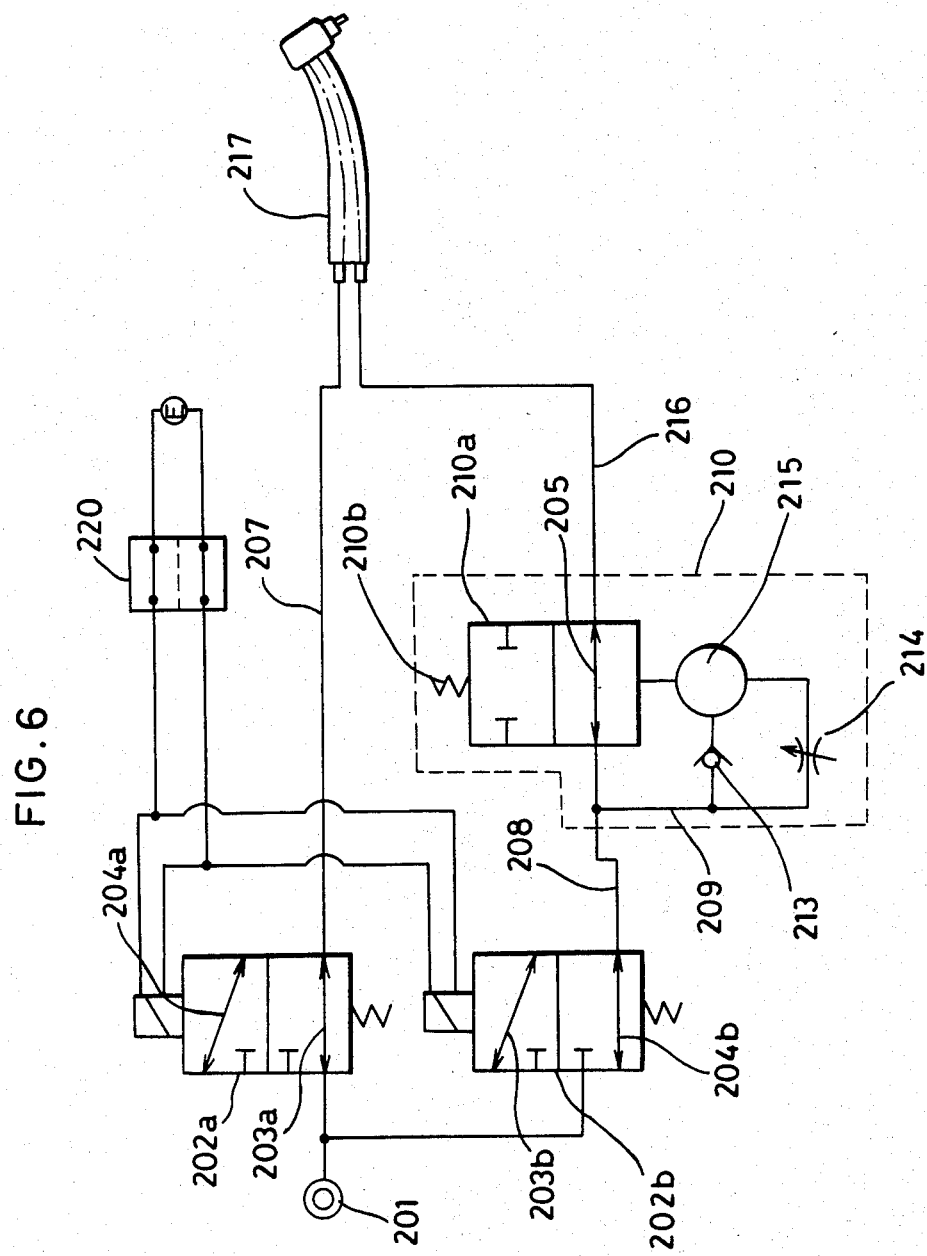
Figure 7:
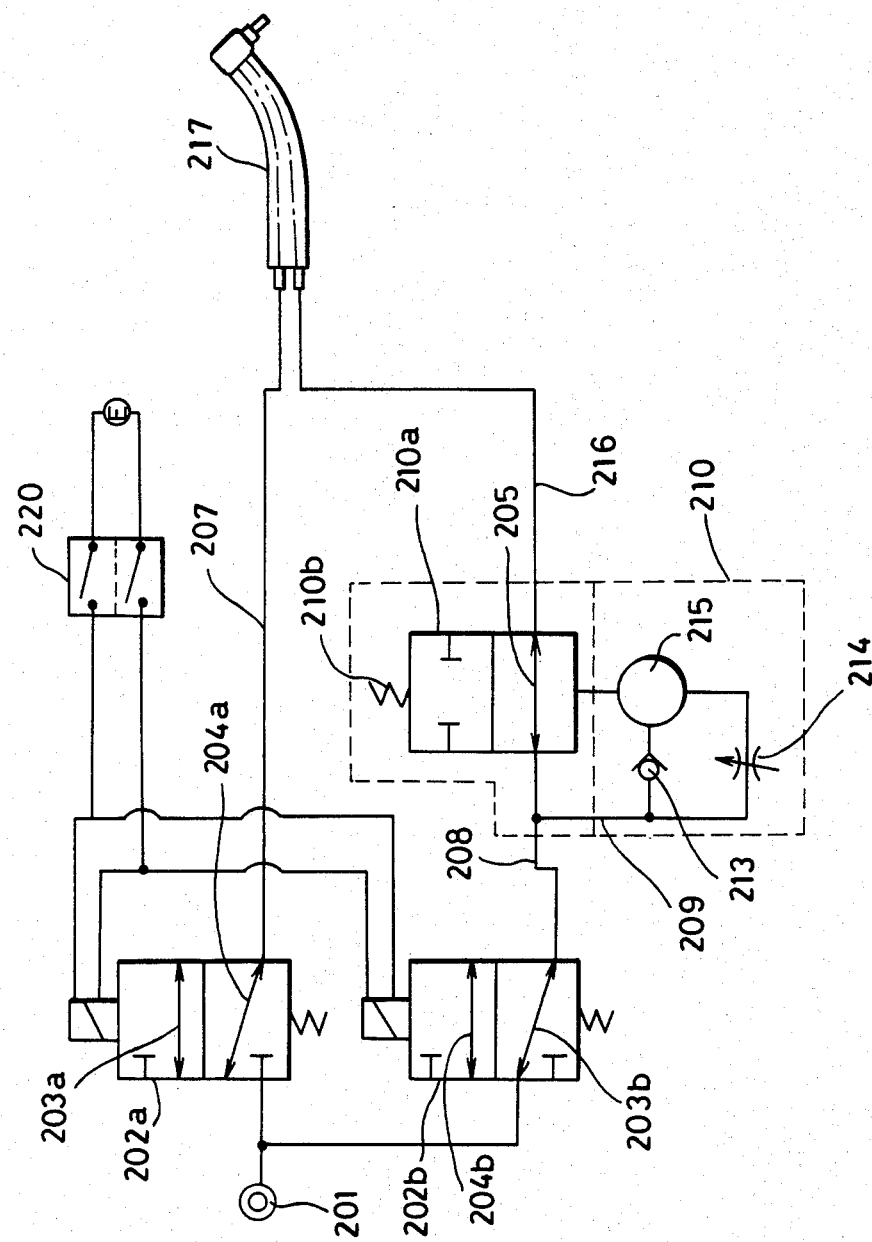

In the embodiment described above, as a means of connecting an air feed passage 107 or air exhaust passage 116 to a compressed air source 101 is employed a four-way magnetic valve 102, but as apparent from FIGS. 5 to 7, the used of a pair of three magnetic valves 202a and 202b operating simultaneously with each other may not be objectionable. Namely, in FIG. 5 showing the state of a handpiece in which the handpiece is placed before it operates, the air feed passage 207 of a handpiece 217 is connected to a compressed air source 201 through a three-way magnetic valve 202a, and a similar exhaust passage 216 is connected to a compressed air source 201 through a closing valve 210a connected to an air timer 210 and through a three-way valve 202b, both magnetic valves 202a and 202b being positioned in series with respect to a switch 220. The construction of the air timer 210 and the closing valve 210a is the same as that shown in FIG. 2.

Accordingly, as apparent from FIG. 5 in the embodiment illustrated, the air feed passage 207 is in communication with a passage 204a to make the passage 204a open to the atmosphere before the handpiece 217 is operated, and the compressed air source 201 is in communication with the tank 215 through passages 203b, 208, 209 and a throttle valve 214 and the internal pressure of the tank 215 overcomes the force of spring 210b to thereby close the closing valve 210a, with the result that compressed air is not supplied to the handpiece 217 and that the handpiece is not rotated. As shown in FIG. 6, when a switch 220 is closed, three-way magnetic valves 202a and 202b are simultaneously operated to thereby not only bring the compressed air source 201 into communication through a passage 203a and air feed passage 207 with the air bearing and turbine of the handpiece 217 to rotate the turbine but also bring passages 208 and 209 into communication with the atmosphere through passage 204b. Accordingly, the compressed air in the tank 215 is instantly released into the atmosphere through a return valve 213 and a throttle valve 214, and the pressure drop in the tank 215 and the force of spring 210b open the closing valve 210a, and the compressed air that passed through the handpiece 217 passes through an exhaust passage 216, passages 205, 208 and 204b and is released into the open air, and thus the turbine continues turning. Then, when the switch 220 is opened, the three-way magnetic valves 202a and 202b are simultaneously returned to the original state as shown in FIG. 7, compressed air is supplied to the handpiece 217 through passages 203b, 208 and 205 and exhaust passages 216 to thereby maintain the inside of the air bearing mechanism at high pressure and urge the turbine to rotate in the opposite direction, with the result that braking force is applied to the turbine. But the compressed air passing through the passage 208 is also supplied to a passage 209 and gradually flows through a throttle valve 214 to the tank 215, and when the internal pressure of the tank 215 has exceeded specified pressure, a closing valve 210a is changed over against the action of spring 210b to thereby produce the state shown in FIG. 5 again, with the result that flow of compressed air to the handpiece 217 completely stops.

In the embodiments described above, changeover between the compressed air source and air feed passage or air exhaust passage is made by the use of a magnetic valve, but substitution of this valve for an air pressure operated changeover valve makes it possible to substitute the entire circuit for an air pressure circuit, and when strictly high responsivity is not required, the described four-way and three-way valves may all be replaced by those capable of being manually changed over. In this case, switches 120 and 220 are not required.

Since the invention, as described above, uses a closing valve controlled by an air timer instead of a switching device for an electric timer operated magnetic valve and applies a braking force to the timer for a certain period of time, the invention is free from deterioration by effect of years or use and instability due to ambient temperature, and in addition, since the opening degree of the throttle valve can optionally be set, the invention makes it possible to optionally set flow time of compressed air for braking the turbine, depending upon air pressure and to control the turbine in a very short time. Accordingly, the invention provides no danger of hurting an operator and reduces production cost. When a brake is applied to the turbine, compressed air is jetted from the rear portion of the turbine, so that the compressed air is applied to the bearing mechanism even during application of the brake, which fact removes the disadvantages of negative pressure created in the bearing mechanism sucking dust or the like thereinto. Also, because control is effected by disposing a closing valve in the exhaust passage, there is not necessity of individually chaging over two magnetic valves as has been the case heretofore. All the changeover valves are simultaneously operated, and movement of the valves are simple, and accordingly, manual operation of the valves is possible, depending upon circumstances.

I claim:

1. A dental turbine rotation control device for a dental air bearing turbine in a static type dental air turbine comprising an air bearing journalling a rotating shaft supporting a dental cutting tool, a turbine provided integral with said shaft, an air passage for supplying said air bearing and turbine with compressed air and an exhaust passage for exhausting air used in said turbine and a compressed air source, said rotation control device being characterized in that it comprises a four-way magnetic valve for connecting said air passage to said compressed air source, a closing valve for opening and closing said exhaust passage, and an air timer for controlling said closing valve, said air timer comprising:

an air tank coupled to said closing valve;
a throttle valve coupling said air tank to said magnetic valve; and
a return valve in parallel with said throttle valve.

* * * * *